United States Patent [19]

Tachi et al.

[11] 4,167,189

[45] Sep. 11, 1979

[54] APPARATUS FOR TRANSMISSION OF INFORMATION BY ELECTROCUTANEOUS STIMULUS

[75] Inventors: Susumu Tachi, Tokyo; Kazuo Tanie, Yokohama, both of Japan

[73] Assignee: Agency of Industrial Science & Technology, Tokyo, Japan

[21] Appl. No.: 781,887

[22] Filed: Mar. 28, 1977

[30] Foreign Application Priority Data

Apr. 26, 1976 [JP] Japan ................................. 51-48112

[51] Int. Cl.$^2$ .............................................. A61N 1/36
[52] U.S. Cl. ......................................... 128/421; 3/1.1
[58] Field of Search ............... 128/404, 419 R, 419 C, 128/419 D, 419 B, 420, 421, 422, 423, 2.1 R, 2.1 Z; 3/1.1

[56] References Cited

U.S. PATENT DOCUMENTS

| | | | |
|---|---|---|---|
| 3,747,605 | 7/1973 | Cook | 128/419 D |
| 3,791,373 | 2/1974 | Winkler et al. | 128/422 X |
| 3,817,254 | 6/1974 | Maurer | 128/421 |
| 3,860,009 | 1/1975 | Bell et al. | 128/419 D |
| 3,869,661 | 3/1975 | Cataigne | 128/2.1 R X |

Primary Examiner—Lee S. Cohen
Attorney, Agent, or Firm—Kurt Kelman

[57] ABSTRACT

In the transmission of information through the medium of electrocutaneous stimuli, the data is generally transmitted by issuing signals in the form of pulse trains which carry the information in terms of their frequency of repetition, the duration time of the train of pulses, the pulse height and the pulse width. Different pulse signals, on conveyance to the organism, generate thereon one and the same magnitude of sensation when the products of pulse widths multiplied by the squares of respective pulse heights are equal. By a procedure of first measuring the cutaneous impedance of a given subject, forwarding the measured value of impedance as a feedback for thereby controlling the pulse signal of the information being transmitted so as to make constant the product of the pulse width multiplied by the square of the pulse height of the pulse signals and passing the controlled pulse signal to the subject, the magnitude of sensation roused in response to any particular signal is rendered constant at all times and therefore the information conveyed through the medium of a varying collection of such particular signals can be correctly transmitted to the subject.

3 Claims, 8 Drawing Figures

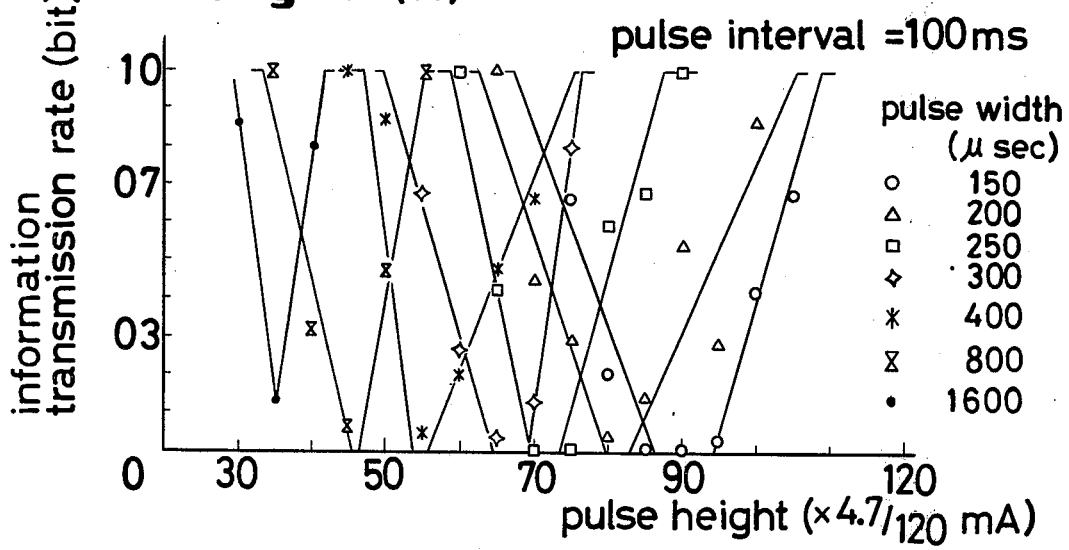
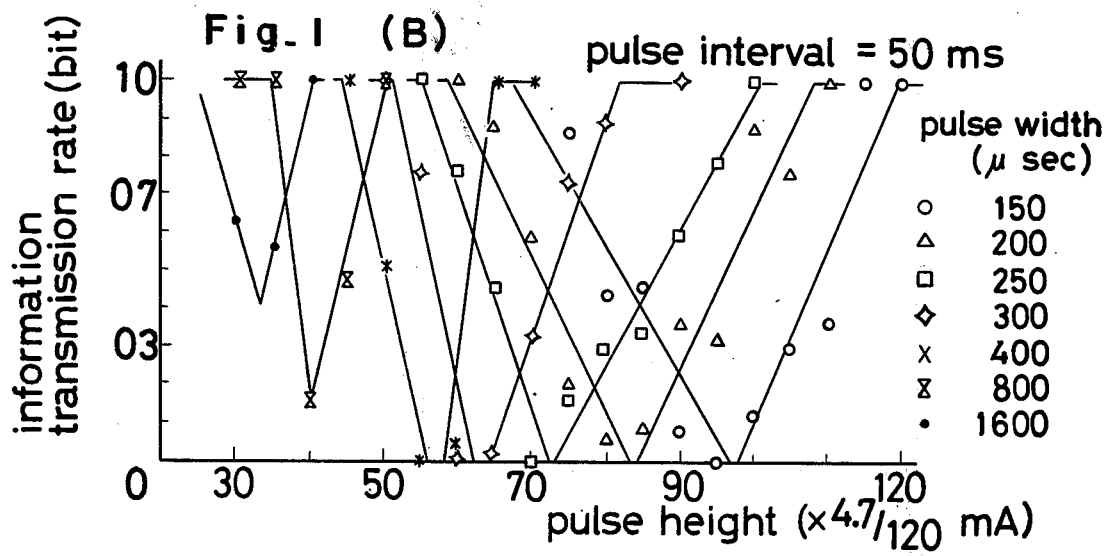
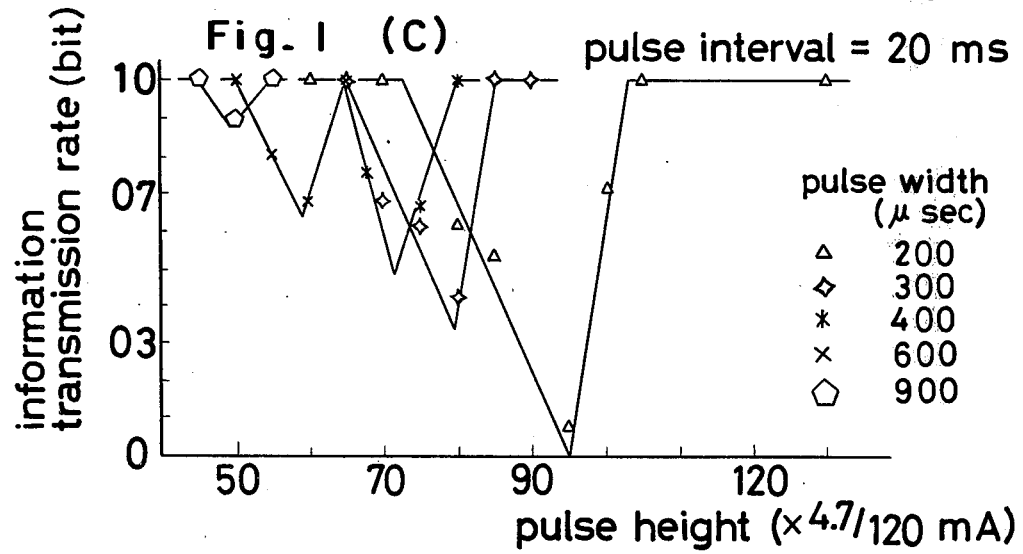

4,167,189

APPARATUS FOR TRANSMISSION OF INFORMATION BY ELECTROCUTANEOUS STIMULUS

BACKGROUND OF THE INVENTION

This invention relates to an apparatus for transmission of information by the medium of electrocutaneous stimuli adapted to rouse the cutaneous sensation of a human subject.

For example, transmission of information through the medium of electrocutaneous stimuli has been adopted in a system wherein the operation of a prosthetic hand or manipulator by its operator is facilitated by feeding back the sensation of touch or sensation of force to the operator with the aid of a device adapted to convey feedback signals from the machine to the operator, in a system which provides the blind or the deaf with a substitutive visual or audio sensation and in a system of communication between two or more individuals under environmental conditions which prevent normal communication.

Such transmission of information through the medium of electrocutaneous stimuli is generally effected by emitting signals in the form of pulse trains which carry the information in terms of their frequency of repetition, stimulus-duration-time, the pulse height (in the form of either voltage or current) and pulse width.

In the conventional system of this type for the transmission of information, signals desired to be conveyed are simply converted into corresponding magnitudes of electric current or some other suitable electric phenomenon and are directly presented to the skin. Because of its anatomical nature, the skin is sometimes moistened with perspiration and at other times is dry, causing a frequent fluctuation in the electrocutaneous impedance. This means that the magnitude of sensation roused by a fixed magnitude of electric current, for example, is likely to vary with time and occasion. This variation has posed a problem in that it prevents the information from being transmitted exactly.

An object of this invention is to provide an apparatus for the transmission of information through the medium of electrocutaneous stimuli, which apparatus is capable of enabling any particular signal to rouse a fixed magnitude of sensation at all times.

SUMMARY OF THE INVENTION

To accomplish the object described above in accordance with the present invention, there is provided a data-transmitting apparatus of the type having electrodes adapted for attachment to the skin of a human subject, applying pulse signals to the electrodes and thereby rousing electrocutaneous stimuli and conveying desired information to the subject, which apparatus comprises means for detecting the cutaneous impedance of the subject, means for controlling the pulse height and pulse width of the pulse signals of the information being transmitted in accordance with the detected cutaneous impedance so as to equalize the product of the square of the pulse height multiplied by the pulse width and means for applying the controlled pulse signals to the electrodes.

It has been ascertained by the inventors that even when a given pulse signals representing a specific item of information has its pulse height or pulse width varied, it is perceived by a human subject as one and the same pulse signal insofar as the product of the square of pulse height multiplied by the pulse width is constant. The possible effect of cutaneous impedance upon the pulse signals can be eliminated and the transmission of information by the pulse signals can be carried out accurately, therefore, by a procedure of preparatorily detecting the cutaneous impedance of the subject, controlling the pulse width or pulse height of the pulse signal in accordance with the detected value so as to bring the product of the square of pulse height multiplied by the pulse width to a constant level and applying the controlled pulse signal to the electrodes.

The other objects and characteristic features of the present invention will become apparent from the description given in detail hereinbelow with reference to the accompanying drawing.

BRIEF DESCRIPTION OF THE DRAWINGS

FIGS. 1(A), 1(B) and 1(C) are graphs showing the relation between the pulse height of the pulse signal and the information transmission rate;

DESCRIPTION OF THE PREFERRED EMBODIMENTS

Figure 2:
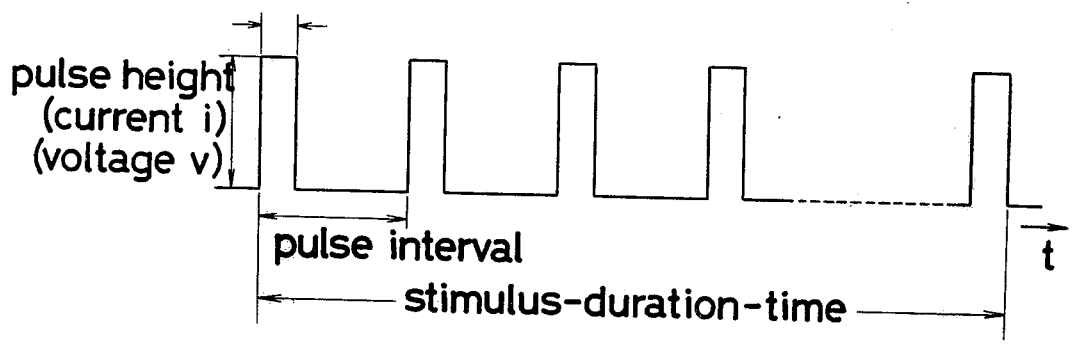
FIG. 2 is a diagram showing the wave form of an electric pulse train conveyed to the skin for generation of electrocutaneous stimuli.

The inventors, with a view to determining the effect of a change in the cutaneous impedance upon the magnitude of sensation roused on the skin by the pulse signal in the transmission of information through the medium of electrocutaneous stimuli, chose three adult subjects, attached electrodes to the upper arm, fixed a standard pulse signal having a pulse width of 100 $\mu$sec and a pulse height of 4.7 mA and varied the pulse width in a signal being compared with said standard pulse signal and randomly applied the standard pulse signal and various pulse signals for comparison each 50 times to the electrodes, with the duration of electrocutaneous stimuli limited to a fixed length of 2 sec, to determine whether the sensation roused by the pulse signal for comparison and that roused by the standard pulse signal are equal or not. The results were as shown in the graphs of FIGS. 1(A), 1(B) and 1(C) wherein the vertical axis is graduated for information transmission rate by a scale wherein 1.0 denotes a case permitting perfect distinction between the standard pulse signal and the pulse signal for comparison and 0 denotes a case permitting absolutely no distinction between the two pulse signals, and the horizontal axis is graduated for pulse height by a scale wherein 120 corresponds to 4.7 mA.

FIG. 1(A) represents the data obtained where the pulse intervals are 100 msec, FIG. 1(B) those obtained where the pulse intervals are 50 msec and FIG. 1(C) those obtained where the pulse intervals are 20 msec.

FIG. 1(A) indicates that, where the pulse width of a signal under comparison is fixed at 200 μsec, the pulse signal can be distinguished perfectly from the standard pulse signal when the pulse height is lower than about 65 or higher than about 105 and can hardly be distinguished when the pulse height is between 80 and 85. It also indicates that where the pulse width of the signal is fixed at 400 μsec, distinction between the pulse signal and the standard pulse signal can be perfectly obtained when the pulse height is lower than about 45 or higher than about 70 and can hardly be obtained when the pulse height is between 55 and 60.

This trend also exists where the pulse intervals are fixed at 50 msec as shown in FIG. 1(B). It is seen that where the pulse intervals are narrowed further to 20 msec (FIG. 1(C)), practically the same trend is observed, though the difference between the pulse signal under comparison and the standard pulse signal becomes clear.

As the result of the experiment described above, it has been ascertained that two pulse signals rouse an equal magnitude of sensation on the organism when the products of their pulse widths (T) multiplied by the squares of their pulse heights (I) are equal.

$$I^2 \cdot T = k \text{ (constant)} \tag{1}$$

The value $I^2$ which is the square of the pulse height (amperage) is proportional to the electric power where the cutaneous impedance Z of the human subject is assumed to be constant.

$$I^2 T \propto Z I^2 T = k \tag{2}$$

wherein $ZI^2T$ denotes the energy which exists while the impedance Z and the amperage I remain absolutely stationary during the period of pulse width T. When an allowance is made for possible variation in the magnitude of amperage during the period, then the relation of Formula (2) will be expressed more exactly as shown in Formula (3).

$$Z \int_O^T i(t)^2 dt \tag{3}$$

wherein i(t) denotes current.

The apparatus for the transmission of information by the present invention has been constructed on the basis of the knowledge described above.

When a particular item of information is to be deposited on the pulse height (amperage), the change in the cutaneous impedance Z is measured in advance and the measured change is compensated for by adjusting the pulse width T. When the information is to be carried on the pulse width T, the change in the cutaneous impedance Z is measured in advance and the measured change is compensated for by adjusting the pulse height I. This compensation permits the magnitude of sensation roused on the skin in response to the signal representing the specific item of data to remain constant and enables the data to be transmitted correctly despite possible change in the cutaneous impedance.

When transmission of data is effected by rousing sensation on the skin of a subject by means of electric stimuli, the signal as the medium of data is given in the form of an electric pulse train of a suitable pulse interval produced over a suitable duration time of stimuli as shown in FIG. 2. In the present invention, when the particular item of information desired to be transmitted is carried on the pulse height (amperage or voltage) or the pulse width, the pulse width or pulse height must be controlled so as to keep the value of Formula (1), preferably Formula (3), constant in order that the magnitude of sensation roused on the skin in response to the signal may be kept at a fixed level.

First in case where the information desired to be transmitted is carried on the magnitude of amperage, the operation starts with measuring the impedance of the skin of the subject. When the measured value is applied to an exactly rectangular pulse, the result is obtained without going through integration, as shown in Formula (4).

$$Z \int_O^T i^2 dt = ZTi^2 \tag{4}$$

Figure 3:
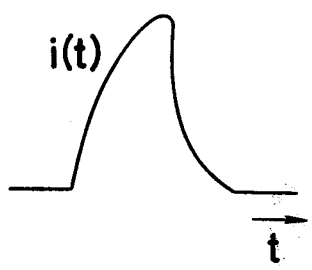
FIG. 3 is a diagram showing one embodiment of the wave form of a modified pulse.

When the cutaneous impedance Z changes to Z', the compensation is obtained by changing the pulse width T of the signal representing the data under transmission so as to satisfy the equation $ZT = Z'T'$, namely, to a value T' which is the quotient of $ZT/Z'$. In case where the wave form is deformed as shown in FIG. 3, the pulse width is controlled so that the value of Formula (3) will have a fixed value as described above.

More strictly, this control is made so as to keep the value of Formula (5) constant.

$$\int_O^T Z(t) \cdot i(t)^2 dt \tag{5}$$

Consequently, the pulse width T is controlled for the electrocutaneous stimuli to be substantially constant regardless of any change in the cutaneous impedance. In the foregoing formula, Z(t) and i(t) denote the cutaneous impedance and the amperage which vary relative to time.

Since the voltage v(t) is the product of $Z(t) \cdot i(t)$, Formula (5) may be replaced by Formula (6) where the voltage v(t) is measurable.

$$\int_O^T i(t) v(t) dt = k \tag{6}$$

In case where the information is carried on the voltage v instead of the amperage, the pulse width T is changed in proportion to the change of cutaneous impedance so as to keep the value of Formula (7), shown below, constant.

$$\frac{1}{Z} \int_O^T v^2 dt \tag{7}$$

When the cutaneous impedance Z changes to Z', the compensation is accomplished by changing the pulse width T to a new value of T' which satisfy the equation $T'/Z' = T/Z$. When the wave form of the signal is deformed, accurate control of the pulse width T for the compensation can be obtained by replacing the values of v and Z with the values v(t) and Z(t) which are variable relative to time as described above.

Figure 4:
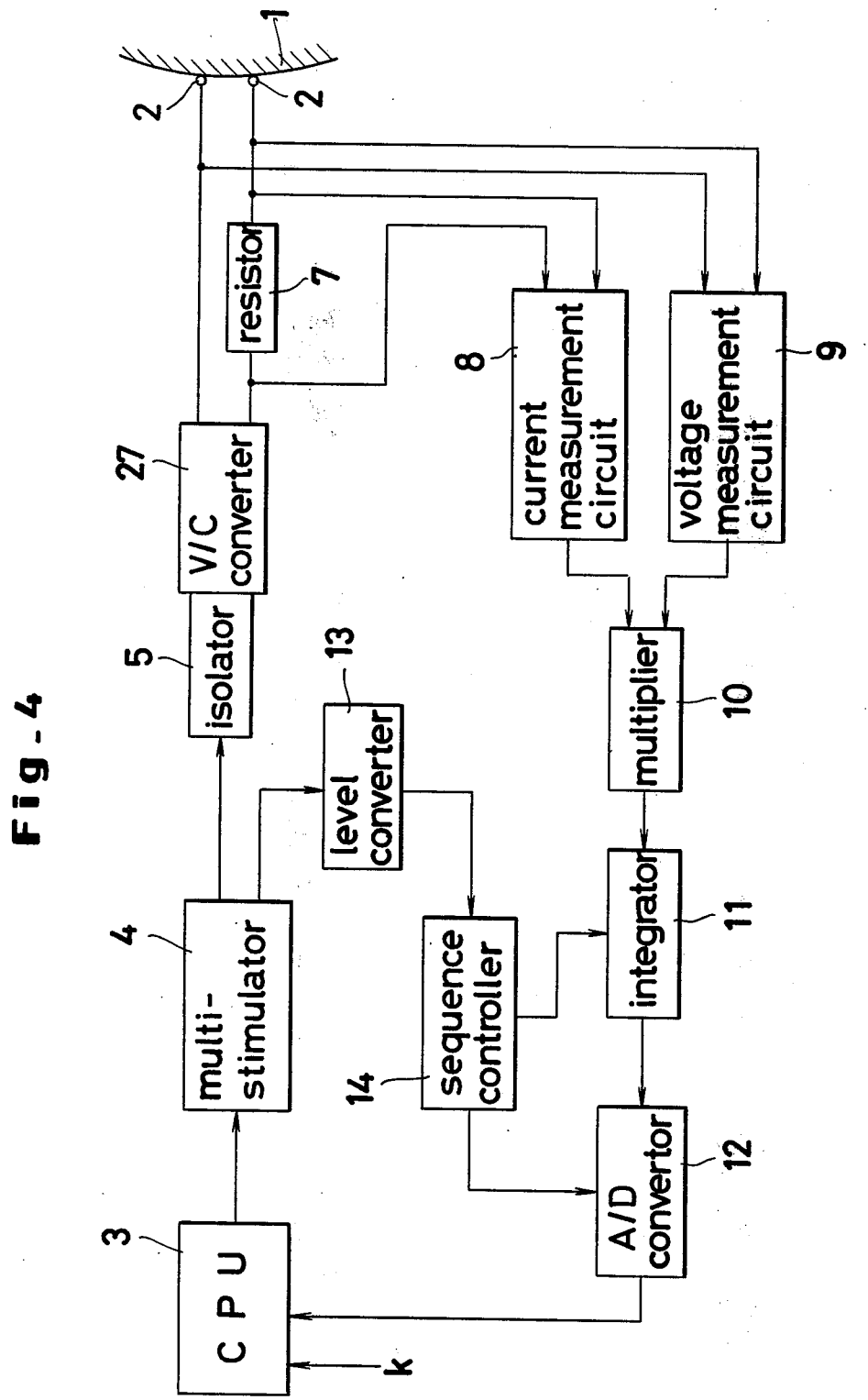
FIG. 4 is a block diagram showing one embodiment of the apparatus for transmission of information according to the present invention.
Figure 5:
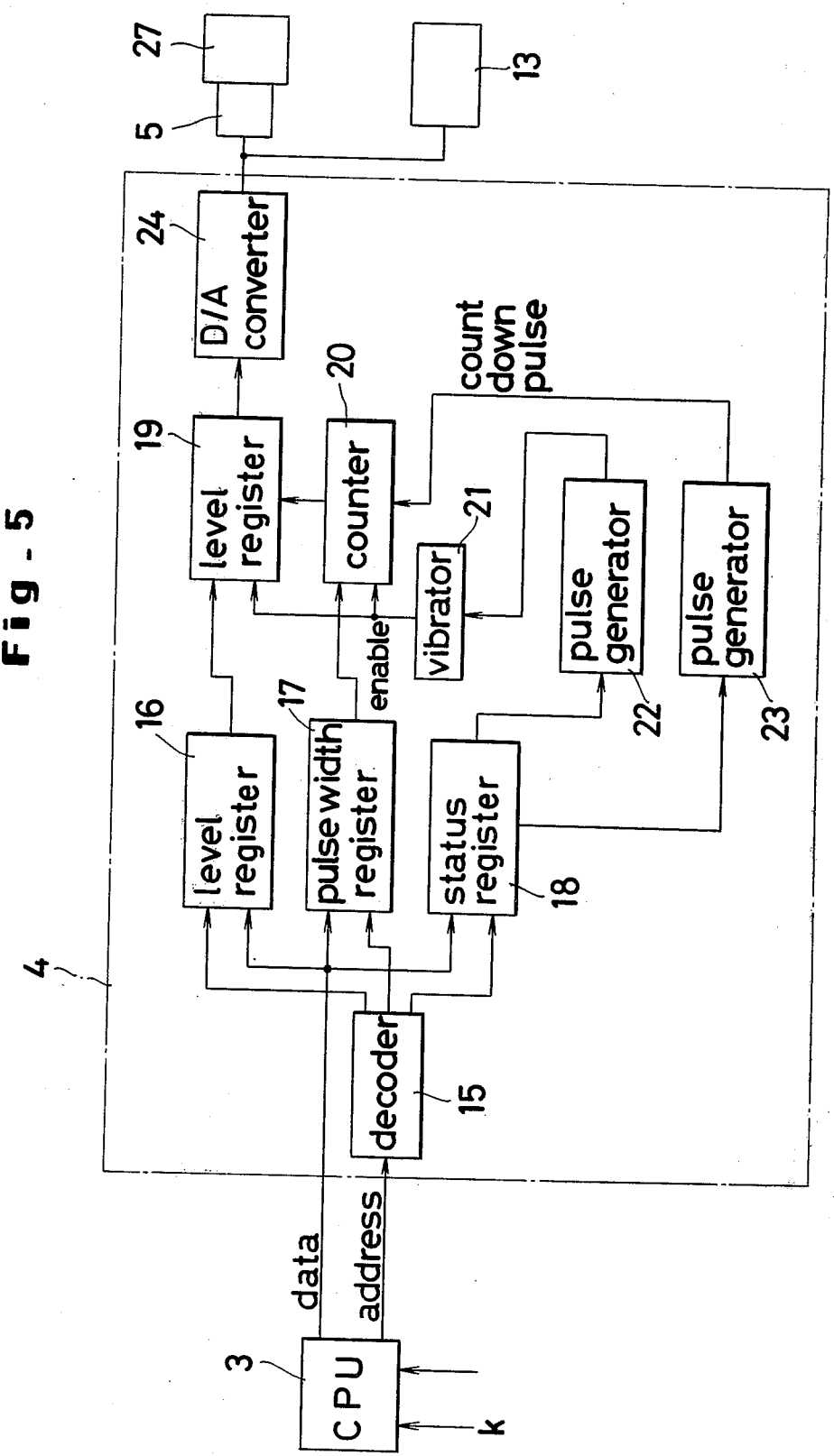
FIG. 5 is a block diagram showing in full detail the multi-stimulator involved in the apparatus of FIG. 4.

FIGS. 4 and 5 are block diagrams illustrating one embodiment of the apparatus for the transmission of information by means of electrocutaneous stimuli according to the present invention, wherein the information to be transmitted is carried on the pulse height. The embodiment will be described by assuming a case wherein the transmission of information is carried out in accordance with the relation of Formula (6). In the case, the value of "k" in the formula represents the information desired to be transmitted.

As the information is forwarded from the CPU (central processing unit) 3 to the multi-stimulator 4 through the data line (FIG. 5), it is selectively fed to the level register 16 (with the pulse height specified) and the pulse width register, depending on the nature of the data. In this case, the allocation of the data to the two registers is accomplished through the medium of the decoder 15 in accordance with the address signal forwarded through the address line. The information allocated respectively to the registers 16 and 17 are not immediately processed to give outputs but are processed by the enable bit of the status register 18. To be specific, when the enable bit is set to "1," the clock pulse generator 22 is started. Consequently the generator 22 issues a pulse to the mono-multi vibrator 21 and actuates the vibrator 21 to give rise to a pulse having a certain width, which is forwarded to the level register 19 and the counter 20. Thus, the information received for temporary storage in the level register 16 and pulse width register 17 are transferred to the level register 19 and the counter 20 respectively. The data now in the level register 19 is directly forwarded to the D/A converter 24. On the other hand, the data received in the counter 20 is deducted by the pulse from the clock pulse generator 23 which is operated by the bit of the status register 18. What is contained in the register 18 is decreased to "0," a borrow signal is issued to the level register 19 to clear what is contained in the register 19. The contents of the register 19, therefore, undergo D/A conversion for the length of time corresponding to the value set in the counter 20, with the result that the multi-stimulator 4 produces as the output a pulse having the amplitude stored in the level register 19 and a width of the value designated in the register 17. This output is applied to the isolator 5. The isolator 5 which is formed of a photo-coupler, for example, drives the battery-powered voltage-current converter 27 to apply an electric current corresponding to the stimulation signal to the pair of electrodes 2 held in contact with or buried in the skin 1 of the subject to whom the data is desired to be transmitted. These electrodes may be either disc-shaped electrodes or needle-shaped electrodes which are known in the art. The circuit 8 for measuring the amperage and the circuit 9 for measuring the voltage are respectively formed by a differential amplifier and an isolator. The amperage of the electric current pulse applied to the electrode 2 is detected by using the differential amplifier of the current-measuring circuit 8 to amplify the voltage drop across the register 7 connected in series between the converter 27 and the electrode 2. The voltage of the electric current pulse is amplified and detected by causing the differential amplifier of the voltage-measuring circuit 9 to be connected to the electrode 2. The magnitude of amperage i(t) detected by the current-measuring circuit 8 and the magnitude of voltage v(t) detected by the voltage-measuring circuit 9 are forwarded through their respective isolators of, for example, photo-coupler type, to the multiplier 10 to be multiplied by each other. The output from the multiplier 10 is integrated by the integrator 11 for the length of time corresponding to the pulse width T. This integrator 11 is provided with a switch adapted to control the three states of integration, hold and reset, with the control effected by means of the control signal issued by the sequence controller 14. By the control signal from the sequence controller 14, an integration signal is forwarded to the integrator. Upon completion of the integration, a hold signal is subsequently issued. At the same time, the sequence controller 14 issues a start pulse to the A/D converter 12 so that the output of the integrator is subjected to A/D conversion by the A/D converter 12. The data resulting from this integration, namely the stimulation energy $$\int_0^T i(t)\, v(t)\, dt$$

per pulse is fed back to the CPU 3.

In the apparatus of the construction described above, when a stimulation energy "k" desired to be transmitted is fed as an input to the CPU 3 through a typewriter (not illustrated), there consequently are established frequency, pulse width and pulse height corresponding to this particular stimulation energy. When one electric current pulse of the established conditions is forwarded as a test signal to the level register 16 and the pulse width register 17 of the multi-stimulator 4, the status register 18 actuates the pulse generators 22 and 23 and the test signal is forwarded from the level register 19 to the electrode 2 via the isolator 5 and V/C converter 27. Since only one pulse is used in this case, virtually no sensation is roused on the subject. The magnitudes of amperage and voltage of the test signal are measured, as described above, by the current-measuring circuit 8 and the voltage-measuring circuit 9 and the product of their outputs is obtained by the multiplier 10, further integrated by the integrator 11, then subjected to A/D conversion by the A/D converter 12 and thereafter fed back to the CPU 3.

Figure 6:
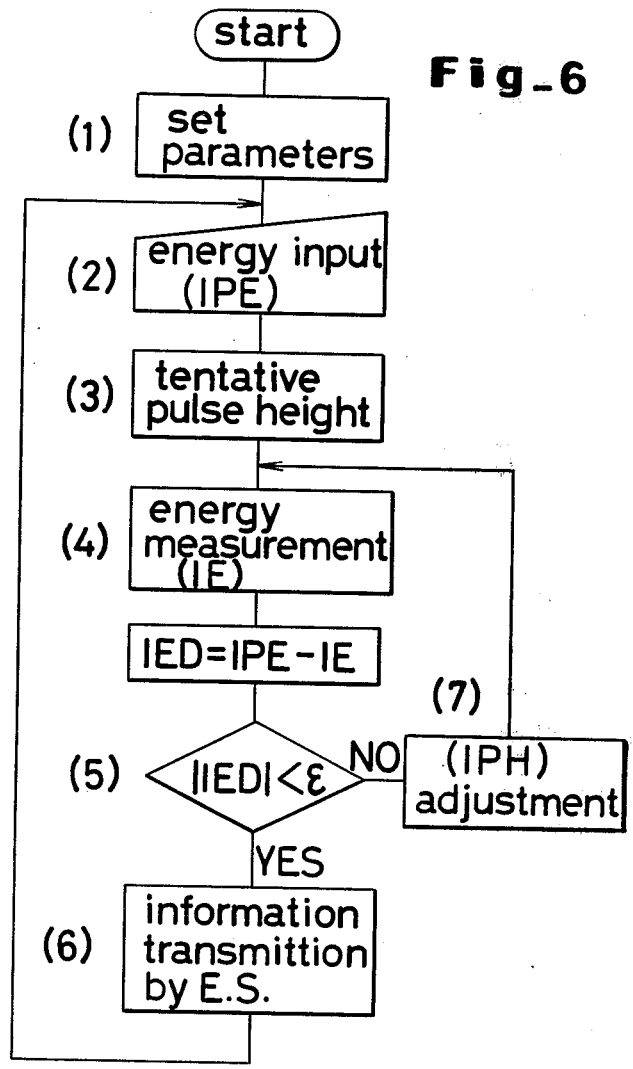
FIG. 6 is an explanatory diagram of the operational process involved in the apparatus for transmission of information according to the present invention.

Within the CPU 3, the value of A/D conversion thus fed back is compared with the established value of energy by an operation such as is illustrated in FIG. 6. The pulse width of the electric current pulse of the signal desired to be transmitted is adjusted on the basis of the cutaneous impedance of the subject.

To be specific, when the parameters of pulse wave form such as number of pulse waves and pulse width of the stimulation energy are established in advance (1) and the data desired to be transmitted is fed (2), then there is established a corresponding pulse IPE. The pulse height IPH of this pulse is calculated from the preparatorily estimated value of cutaneous impedance. The resultant pulse is forwarded as a test pulse to the electrodes set on the subject (3). The pulse width IPW of this initial test current pulse is calculated, for example, in accordance with the following formula.

$$IPH = c\sqrt{IPE} \qquad (8)$$

wherein, c denotes a variable parameter.

The magnitudes of amperage and voltage of the electric current pulse forwarded to the subject are measured. The product of the magnitudes is integrated and the result of the integration undergoes A/D conversion (4). The result of this conversion IE is fed back to the CPU to be compared with the initially set pulse IPE ($IPE - IE = IED$), with the result that the difference IED from the electric current pulse IPE desired to be transmitted (5). When the difference IED thus determined is smaller than the allowable value $\epsilon$ of the pulse strength perception by the human being (5), this electric current pulse is forwarded as the actual data to the electrodes for a prescribed length of time, effecting the transmission of data (6). When the difference IED happens to be greater than the allowable value, the pulse signal has its pulse height IPH changed once again and, in the resultant modified form, forwarded as a test pulse to the subject so as to find the measured value IE and determine whether or not the difference IED from the electric current pulse IPE desired to be transmitted falls below the allowable value $\epsilon$. The correction of the pulse height IPH is repeated until the difference decreases below the allowable value. At the time that the difference becomes smaller than the allowable value $\epsilon$, the electric current pulse resulting from the final correction is given as the signal for transmission of data to the subject for a prescribed length of time. In this case, the correction of pulse height is carried out in accordance with the following formula, for example.

$$IPH = c\sqrt{|IPE - IE|} \quad (9)$$

In case where the pulse width IPW is changed by way of compensation instead of the change of pulse height IPH, the pulse width is changed in accordance with the following formula, for example, while the amplitude of the electric current is kept at its initial value. The modified value of the pulse width is forwarded to the pulse width register 17. From this point onward, the procedure applicable to the compensation by the change of pulse height will be followed.

$$IPW = IPW \pm c(IPE - IE) \quad (10)$$

The preceding embodiment has been described as effecting the modification of pulse height or pulse width by use of a computer operated on the digital basis. Alternatively, the modification may be accomplished on the analogous basis with the aid of exclusive circuits.

First, transmission of data as carried by the pulse height will be described.

Figure 7:
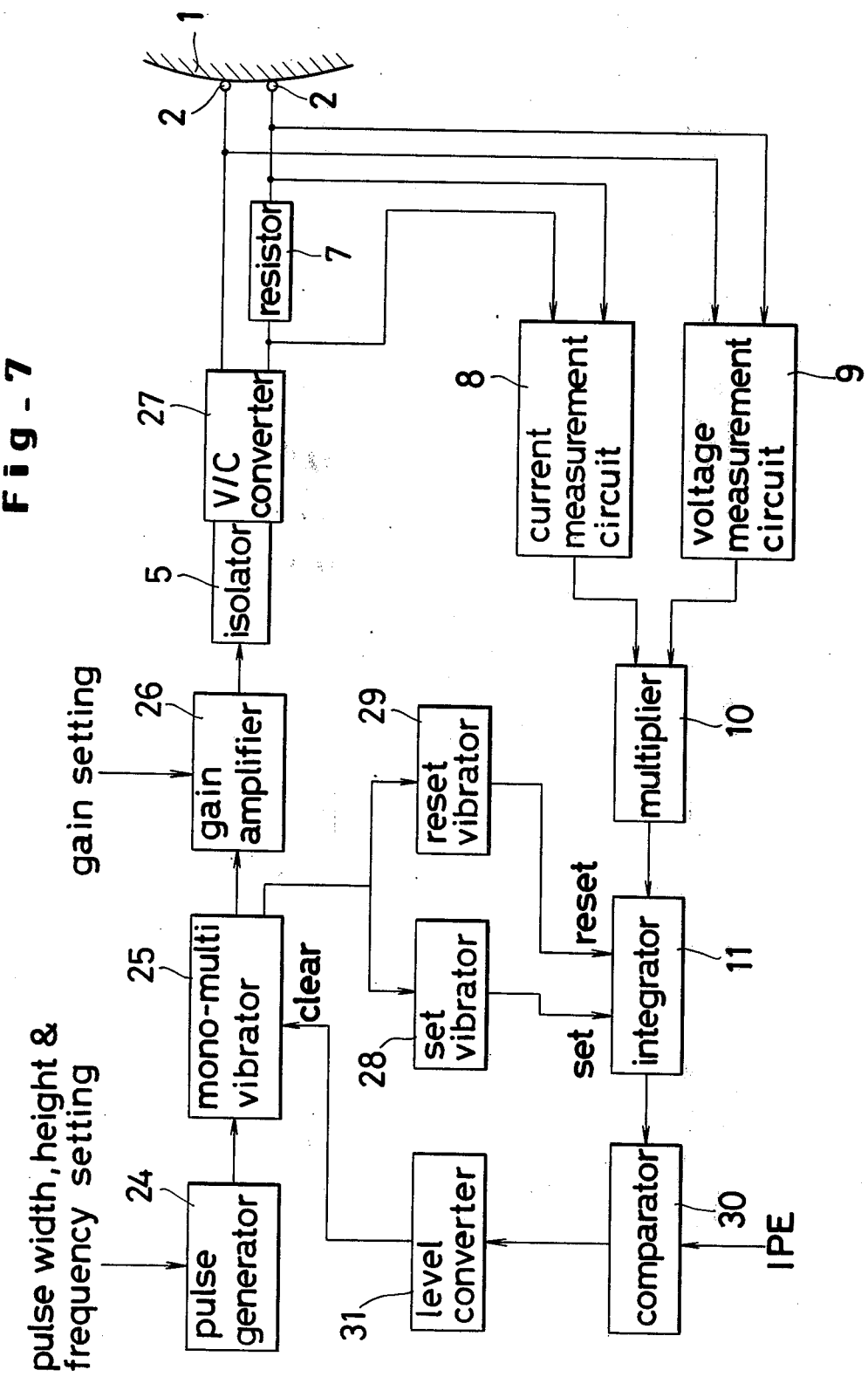
FIGS. 7 and 8 are block diagrams illustrating other embodiments of the apparatus for transmission of information according to the present invention.

With reference to FIG. 7, one pulse signal having preparatorily established pulse height, pulse width and pulse interval is issued from the pulse generator 24 to the mono-multi vibrator 25 provided with clear terminals. The output of the vibrator 25 is forwarded to the variable gain amplifier 26 and converted into a pulse train having a pulse height to be established by an external gain signal. The pulse train is forwarded to the isolator 5. The isolator 5 drives the battery-powered voltage-current converter 27 to apply an electric current corresponding to the stimulation pulse to the pair of the electrodes 2 fastened to the skin.

The magnitudes of amperage and voltage of the electric current just mentioned are measured by the current-measuring circuit 8 provided with an isolator and the voltage-measuring circuit 9 provided with an isolator in much the same way as in the embodiment illustrated in FIG. 4. The output of these measuring circuits 8, 9 are multiplied by each other in the multiplier 10 and thereafter integrated by the integrator 11. As the signal for starting this integration by the integrator 11, the rising portion of the output pulse of the mono-multi vibrator 25 is processed by the mono-multi vibrator 28 (front edge trigger type) and forwarded to the integrator 11. The output of the integrator 11 is compared with the signal IPE desired to be transmitted at the comparator 30. The comparator 30 issues a pulse when the output of the integrator 11 is greater than the signal IPE. This pulse is forwarded to the level converter 31, in which it is converted to a pulse signal of the prescribed level. The output of the level converter 31 is applied to the clear terminal of the monostable multivibrator 25, with the result that the output of the monostable multi-vibrator 25 is cleared. Consequently, the stimulation electric current to the isolator 5 falls to 0, producing as the output a pulse having an energy of the magnitude designated by the signal IPE. The integrator 11 functions to cause the rising portion of the output pulse of the mono-multi vibrator 25 to be reset with the signal which has been processed by the monostable multi-vibrator 29 (rear edge trigger type).

Now, the preceding embodiment will be described with reference to concrete numerical values. It is assumed that the stimulation current which is the output of the variable gain amplifier 26 is fixed at a pulse height of 5.0 mA, the cutaneous impedance (taken as consisting of pure resistance elements) is fixed at 1 K$\Omega$ and the magnitude of signal IPE is fixed at 30 erg. Then the output $I_{out}$ of the integrator 11 is expressed by the following equation.

$$I_{out} = \int_O^T \{(5.0 \times 10^{-3})^2 \times (1 \times 10^3)\} dt \times 10^7 =$$
$$2.5 \times 10^4 t (\text{erg})$$

wherein, T denotes the interval of pulse and t the pulse width.

So, the pulse width t is to be adjusted so that the difference between the value found by the foregoing equation and the signal value IPE is brought to 0. That is to say, the comparator 30 issues an output when the following expression is satisfied.

$$2.50 \times 10^4 T - 30 \leq 0$$

This formula states that upon integration $T = 1.2 \times 10^{-4}$ sec = 120 $\mu$s, the output of the integration circuit 11 exceeds the target value IPE (= 30 erg), at which time the comparator 30 issues an output to clear the output of the monostable multi-vibrator 25, and that as the result the stimulation current is brought down to 0. Thus, the pulse width is adjusted to 120 $\mu$s when the target value of 30 erg is given.

Now, transmission of information as carried by the pulse width will be described with reference to FIG. 8.

Figure 8:
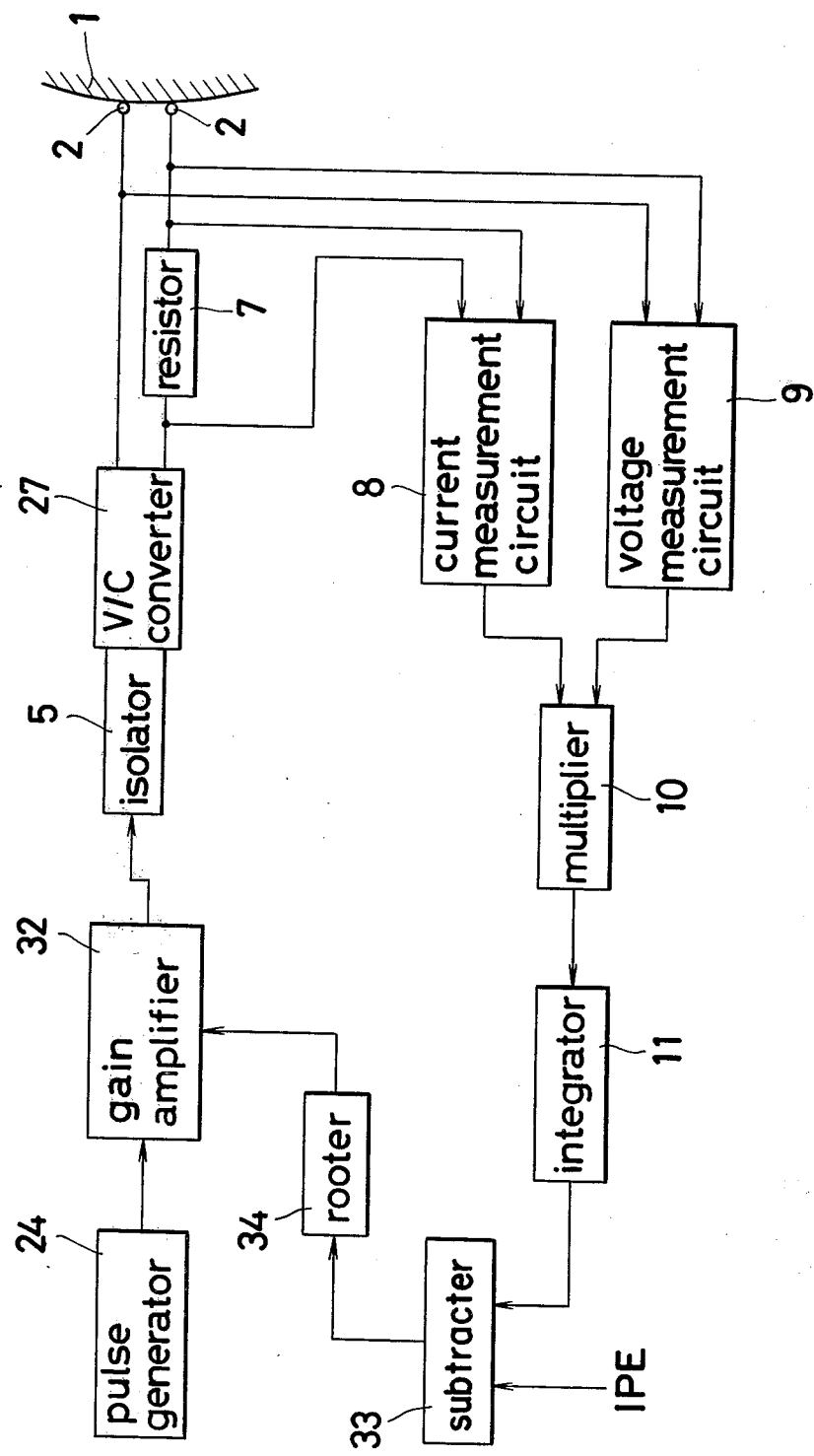

In FIG. 8, the pulse generator 24 issues as the test pulse one voltage pulse having prescribed pulse height and pulse width. This test pulse is forwarded to the isolator 5 through the medium of a variable gain amplifier 32, which causes the battery-powered voltage-amperage converter 27 to produce an electric current corresponding to the test pulse signal and apply said electric current to the electrodes 2. The magnitudes of amperage and voltage of the electric current are measured by the current-measuring circuit 8 and the voltage-measuring circuit 9 respectively. The outputs of these measuring circuits are multiplied by each other by the multiplier 10 and the resultant product is integrated by the integrator 11. The subtractor 33 outputs the difference between the result of this integration and the electric current pulse corresponding to the signal IPE desired to be transmitted and the difference is processed by the rooter 34 to extract the square root thereof. The square root of the difference is fed back to the variable gain amplifier 32. The variable gain amplifier 32 issues an output having a pulse height corresponding to the output of the rooter 34.

The preceding embodiment will now be explained by using concrete numerical values. It is assumed that the magnitude of signal IPE desired to be transmitted is fixed at 30 erg, the cutaneous impedance is fixed at 1 KΩ and the pulse width of the pulse signal of stimulation is fixed at 100 μs. Similarly to the preceding embodiment, the output of the integrator 11 is expressed as follows.

$$I_{out} = \int_0^T \{(IPH)^2 \times (1 \times 10^3)\}dt \times 10^7 =$$
$$(IPH)^2 \times 10^3 \times (100 \times 10^{-6}) \times 10^7 (erg)$$

wherein T denotes the cycle of pulse and IPH the pulse height. Consequently, the output of the subtraction circuit 33 is expressed as follows.

$$I_{out} - 30 = (IPH)^2 \times 10^6 - 30$$

The output of the rooter 34 is obtained as follows.

$$\sqrt{(IPH)^2 \times 10^6 - 30}$$

The output of the amplifier 32 is adjusted so that the output of the rooter 34 will be brought down to 0. That is to say, the adjustment is made so that the IPH is brought to 5.5 mA ($=5.5 \times 10^{-3}$).

As described above, the apparatus for the transmission of information according to the present invention eliminates the effect of cutaneous impedance and therefore enables one and the same signal representing the information to rouse a constant magnitude of sensation on the skin of the subject at all times. Thus, the information can be accurately transmitted.

Now the program for effecting the present invention by use of a computer, PAP 11/40, will be expressed by the conventional Fortran computer language.

```
            IPW=2
            IPI=20
            IST=2000
            IPH=100
            EK=4.0
            AIK=0.1
            ICN=1
            ITPRM=50
            ICN2=0
            IF(ICN. EQ. 0) ICN2=1
            IST1=(IST*ICN2*10+IST*ICN)/IPI
   10       CONTINUE
            READ (5, 501) IPE
   501      FORMAT(13)
            IPH=SQRT(EK*FLOAT(IPE)/FLOAT(IPW))
            IF(IPH. GT. 255) IPH=255
            IT=IPE/ITPRM
   4004     CALL DELAY2
            CALL DAOUT6 (IPW, IPH, ICN, IPI, IE)
            IED=IPE-IE
            IF(IABS(IED). LT. IT) GO TO 4005
            IF (IED. LT. 0) GO TO 4102
            IK=SQRT(FLOAT(IED)*AIK)
            IPH=IPH+IK
            IF(IPH. GT. 255) IPH=255
            IF(IPH. LT. 0) IPH=0
            GO TO 4004
   4102     IED=IABS(IED)
            IK=SQRT(IABS(IED)*AIK)
            IPH=IPH-IK
            IF(IPH. GT. 255) IPH=255
            IF(IPH. LT. 0) IPH=0
            GO TO 4004
   4005     CALL DELAY
            CALL DAOUT (IPW, IPH, ICN, IPI, IST1)
            CALL DELAY
            GO TO 10
            STOP
            END
            SUBROUTINE DELAY
            DO 10 I=1, 10000
            DO 11 J=1, 4
            I=I
            J=J
   11       CONTINUE
   10       CONTINUE
            RETURN
            END
            SUBROUTINE DELAY2
            DO 10 I=1, 6000
            I=I
   10       CONTINUE
            RETURN
            END
            .GLOBL      DAOUT6
            .MCALL      ..V2..,.REGDEF
            ..V2..
            .REGDEF
   DRDB=    172416
   DRWC=    172410
   DRST=    172414
   DRBA1=   172412
   DRBA2=   177000
   DACST=   177002
   FPR1=    174000
   PSW=     177776
   LKS=     177546
            .CSECT
   DAOUT6:  MOV         SP, SPSAVE
            MOV         LKS, LKSSAV
            MOV         PSW, PSWSAV
            MOV         @#124, S1
            MOV         @#126, S2
            CLR         @#170404
            CLR         LKS
            MOV         #17, FPR1
            CLR         R1
            CLR         R2
            CLR         DRDB
            CLR         DRWC
            CLR         DRST
            CLR         DRBA1
            CLR         DRBA2
            CLR         DACST
            CLR         COUNT
            MOV         #20, @#170400
            MOV         #INTDAC, @#354
            MOV         #340, @#356
            MOV         #INTDMA, @#124
            MOV         #300, @#125
            MOV         (R5)+, R1
            MOV         @(R5)+, R1
            ASH         #10, R1
            MOV         R1, R2
            ADD         @(R5)+, R1
            MOV         R1, DRDB
            MOVB        #0, DRDB
            MOVB        #1, DRDB
            ADD         #140, R2
            MOV         R2, DRDB
            MOVB        #2, DRDB
            MOVB        #3, DRDB
            MOV         @(R5)+, R1
            TST         R1
            BEQ         MIC
   MIL:     MOV         @(R 5)+, R1
            ASH         #6, R1
            ADD         #62, R1
            MOV         R1, DACST
            MOV         @(R5), IST
            JMP         DAGO
   MIC:     MOV         @(R5)+, R1
```

-continued

```
            ASH     #6, R1
            ADD     #42, R1
            MOV     R1, DACST
            JMP     DAGO
DAGO:       INC     DACST
DAWT:       WAIT
            JMP     DAWT
INTDAC:     INC     COUNT
            CMP     COUNT, #3
            BEQ     DASTP
LOOP1:      TSTB    @#170400
            BPL     LOOP1
            MOV     @#170402, R0
            RTI
DASTP:      TSTB    @#170400
            BPL     DASTP
            MOV     @#170402, @(R5)
            CLR     FPR1
            CLR     R0
LOOP2:      INCB    R0
            BVC     LOOP2
            CLR     DRST
            CLR     DACST
            MOV     SPSAVE, SP
            MOV     PSWSAV, PSW
            MOV     LKSSAV, LKS
            MOV     S1, @#124
            MOV     S2, @#126
            RTS     PC
INTDMA:     HALT
IST:        0
COUNT:      0
SPSAVE:     0
LKSSAV:     0
PSWSAV:     0
S1 :        0
S2 :        0
            .END
            .GLOBL  DAOUT
            .MCALL  ..V2..,.REGDEF
            ..V2..
            .REGDEF
DRDB=       172416
DRWC=       172410
DRST=       172414
DRBA1=      172412
DRBA2=      177000
DACST=      177002
FPR1=       174000
PSW=        177776
LKS=        177546
            .CSECT
DAOUT:      MOV     SP, SPSAVE
            MOV     LKS, LKSSAV
            MOV     PSW, PSWSAV
            MOV     @#124, S1
            MOV     @#126, S2
            MOV     #17, FPR1
            CLR     R1
            CLR     DRDB
            CLR     DRWC
            CLR     DRST
            CLR     DRBA1
            CLR     DRBA2
            CLR     DACST
            CLR     COUNT
            MOV     #INTDAC, @#354
            MOV     #340, @#356
            MOV     #INTDMA, @#124
            MOV     #300, @#126
            MOV     (R5)+, R1
            MOV     @(R5)+, R1
            ASH     #10, R1
            MOV     R1, R2
            ADD     @(R5)+, R1
            MOV     R1, DRDB
            MOVB    #0, DRDB
            MOVB    #1, DRDB
            ADD     #200, R2
            MOV     R2, DRDB
            MOVB    #2, DRDB
            MOVB    #3, DRDB
            MOV     @(R5)+, R1
            TST     R1
```

-continued

```
            BEQ     MIC
MIL:        MOV     @(R5)+, R1
            ASH     #6, R1
            ADD     #62, R1
            MOV     R1, DACST
            MOV     @(R5), IST
            JMP     DAGO
MIC:        MOV     @(R5)+, R1
            ASH     #6, R1
            ADD     #42, R1
            MOV     R1, DACST
            MOV     @(R5), IST
            JMP     DAGO
DAGO:       INC     DACST
DAWT:       WAIT
            JMP     DAWT
INTDAC:     INC     COUNT
            CMP     COUNT, IST
            BEQ     DASTP
            RTI
DASTP:      CLR     FPR1
            MOV     SPSAVE, SP
            MOV     PSWSAV, PSW
            MOV     LKSSAV, LKS
            MOV     S1, @#124
            MOV     S2, @#126
            RTS     PC
INTDMA:     HALT
IST:        0
COUNT:      0
SPSAVE:     0
LKSSAV:     0
PSWSAV:     0
S1 :        0
S2 :        0
            .END
```

What is claimed is:

1. In an apparatus for the transmission of information, comprising means for applying pulse signals representing a desired item of information to electrodes fastened to the skin of a human subject for thereby transmitting the information by electro-cutaneous stimuli, an improvement which comprises (a) the means for applying pulse signals including means for applying pulse signals corresponding to stimulation energy based on the information to be transmitted, (b) means for measuring the current and voltage of the pulse signals corresponding to stimulation energy for thereby detecting the cutaneous impedance of the human subject, (c) the means for applying pulse signals including means for applying pulse signals on the basis of the detected cutaneous impedance, (d) means for controlling the pulse signals so that the product of the square of pulse height multiplied by pulse width of the pulse signals corresponding to stimulation energy is equal to the product of the square of the pulse height multiplied by pulse width of the pulse signals on the basis of the detected cutaneous impedance, and (e) the means for applying the pulse signals including means for applying the controlled pulse signals to the electrodes.

2. The apparatus for the transmission of information according to claim 1, comprising means for controlling the pulse height of the pulse signal so as to make constant the product of the square of pulse height multiplied by the pulse width of the pulse signals representing the data desired to be transmitted.

3. The apparatus for the transmission of information according to claim 1, comprising means for controlling the pulse width of the pulse signal so as to make constant the product of the square of pulse height multiplied by the pulse width of the pulse signals representing the data desired to be transmitted.

* * * * *